(12) United States Patent
Ramesha et al.

(10) Patent No.: US 9,334,240 B2
(45) Date of Patent: May 10, 2016

(54) METHOD OF PREPARATION OF IMIPRAMINE PAMOATE AND NOVEL CRYSTALLINE FORM OF IMIPRAMINE PAMOATE THEREOF

(71) Applicant: R L Fine Chem, Bangalore (IN)

(72) Inventors: Andagar Ramakrishna Ramesha, Bangalore (IN); Anjan Kumar Roy, Bangalore (IN)

(73) Assignee: R.L. FINE CHEM, Bangalore (IN)

( * ) Notice: Subject to any disclaimer, the term of this patent is extended or adjusted under 35 U.S.C. 154(b) by 125 days.

(21) Appl. No.: 14/259,839

(22) Filed: Apr. 23, 2014

(65) Prior Publication Data

US 2015/0225349 A1    Aug. 13, 2015

(30) Foreign Application Priority Data

Feb. 13, 2014  (IN) .............................. 671/CHE/2014

(51) Int. Cl.
*C07D 223/28* (2006.01)
*C07D 223/26* (2006.01)
*C07C 51/43* (2006.01)

(52) U.S. Cl.
CPC .............. *C07D 223/26* (2013.01); *C07C 51/43* (2013.01)

(58) Field of Classification Search
CPC ..................................................... C07D 223/28
USPC .......................................................... 540/592
See application file for complete search history.

(56) References Cited

U.S. PATENT DOCUMENTS 7,718,649 B1    5/2010   King et al.
8,039,461 B1    10/2011  Audia et al.

FOREIGN PATENT DOCUMENTS

WO    WO 2009/047796 A1    4/2009

*Primary Examiner* — Brenda Coleman
(74) *Attorney, Agent, or Firm* — Oliff PLC

(57) ABSTRACT

The present invention is in relation to preparation of Imipramine Pamoate by a simple two-step process. The process provides new form of Imipramine Pamoate. The present invention is cost effective, involves mild conditions to beget said compound.

10 Claims, 4 Drawing Sheets

METHOD OF PREPARATION OF IMIPRAMINE PAMOATE AND NOVEL CRYSTALLINE FORM OF IMIPRAMINE PAMOATE THEREOF

TECHNICAL FIELD

The present disclosure is in relation to the preparation of tricyclic antidepressant, Imipramine Pamoate. The present disclosure provides a one pot preparation of Imipramine Pamoate in high yield with high purity. The amiable conditions and cost effective reagents renders to beget the compound economically.

BACKGROUND AND PRIOR ART 3-(10,11-Dihydro-N,N-dimethyl-5H-dibenz[b,f]azepine-5-propanamine) commonly known as Imipramine is a well-known tricyclic medicant. The hydrochloride salt and Pamoate salt of imipramine are widely used with common names Tofranil and Tofranil-PM respectively. While Tofranil is prescribed as medication for both depression and enuresis, Tofranil-PM is specifically used as antidepressant.

Tofranil-PM, represented by the formula-1 is a dipamoate salt of Imipramine. Considering the potential of Imipramine Pamoate, many methods have been developed for its preparation.

Formula-1

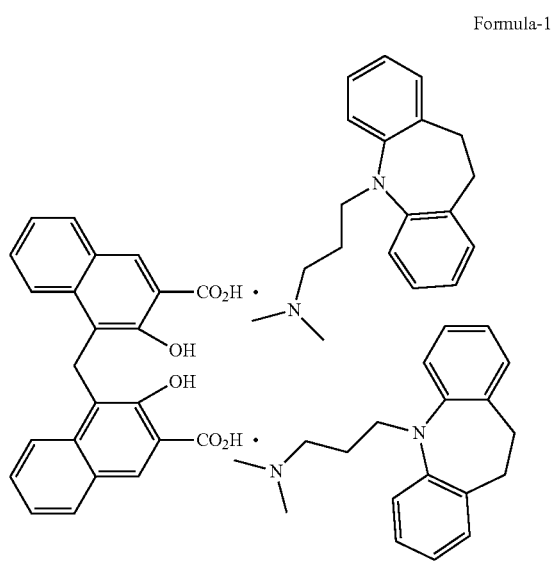

The synthesis described in, U.S. Pat. No. 7,718,649 describes a synthesis of amorphous forms of Imipramine Pamoate from disodiumpamoate with Imipramine hydrochloride in aqueous solution. WO2009/047796 gives the preparation of crystalline form of Imipramine Pamoate using disodium Pamoate with Imipramine Hydrochloride in aqueous solution. U.S. Pat. No. 8,039,461, describes conversion of known forms of polymorphs of Imipramine Pamoate to other polymorphic forms by heating and further processing the product obtained.

It can be noted that aforementioned procedures utilize Sodium Pamoate and water solvent as Pamoic acid is poorly soluble in many of the common organic solvents.

Apart from the methods being tedious the usage of sodium salt of Pamoic acid leads to the contamination of the product with sodium chloride and usage of water may lead to microbial contamination. The methods are also tedious with multiple steps and requires surplus amount of reagents to obtain the target compound. The yield of the target compound is not appreciable making the entire process uneconomical.

In order to reduce the cost of Imipramine Pamoate it is imperative that a simple method with cost effective reagents is proposed. The present disclosure provides an economical method with high yield clearly demonstrating to aid in reduction of the cost of the target compound.

STATEMENT OF DISCLOSURE

Accordingly the present invention provides a method for preparation of Imipramine Pamoate, said method comprising acts of, a) reacting Pamoic acid and Imipramine in a solvent and stirring to obtain Imipramine Pamoate solution; and b) filtering or distilling the solution to obtain the Imipramine Pamoate; and novel polymorphic crystalline form of Imipramine Pamoate.

DETAILED DESCRIPTION OF DISCLOSURE

The present invention is in relation to a method for preparation of Imipramine Pamoate, said method comprising acts of, a) reacting Pamoic acid and Imipramine in a solvent and stirring to obtain Imipramine Pamoate solution; and b) filtering or distilling followed by precipitating to obtain the Imipramine Pamoate from the solution.

In another embodiment of the present invention, the method is a single or multiple pot preparation, preferably single pot preparation.

In still another embodiment of the present invention, the Pamoic acid and the Imipramine are taken in a ratio ranging from about 2:1 to about 4:1.

In yet another embodiment of the present invention, the solvent is selected from a group comprising dichloromethane, ethylacetate, isopropylacetate, methyl ethyl ketone, acetone and combination thereof.

In yet another embodiment of the present invention, the stirring is carried out for a period ranging from about 12 hr to about 16 hr.

In yet another embodiment of the present invention, wherein the stirring is carried out at a temperature ranging from about 20° C. to about 50° C.

In yet another embodiment of the present invention, the Imipramine Pamoate is filtered if the solvent is the ethylacetate.

In yet another embodiment of the present invention, the Imipramine Pamoate is precipitated by acetone or ethyl acetate if the solvent is the dichloromethane.

In yet another embodiment of the present invention, the Imipramine Pamoate is of purity ranging from about 99.7% to about 99.9%

The present invention is also in relation to novel polymorphic crystalline form of Imipramine Pamoate as characterised by Fourier transform infrared spectrum and X-ray powder diffraction method.

An embodiment of the present invention provides a method of preparation of Imipramine Pamoate comprising two simple steps of reacting Imipramine base and Pamoic acid to obtain Imipramine Pamoate and later separating the said compound from the reaction mixture.

Figure 1:
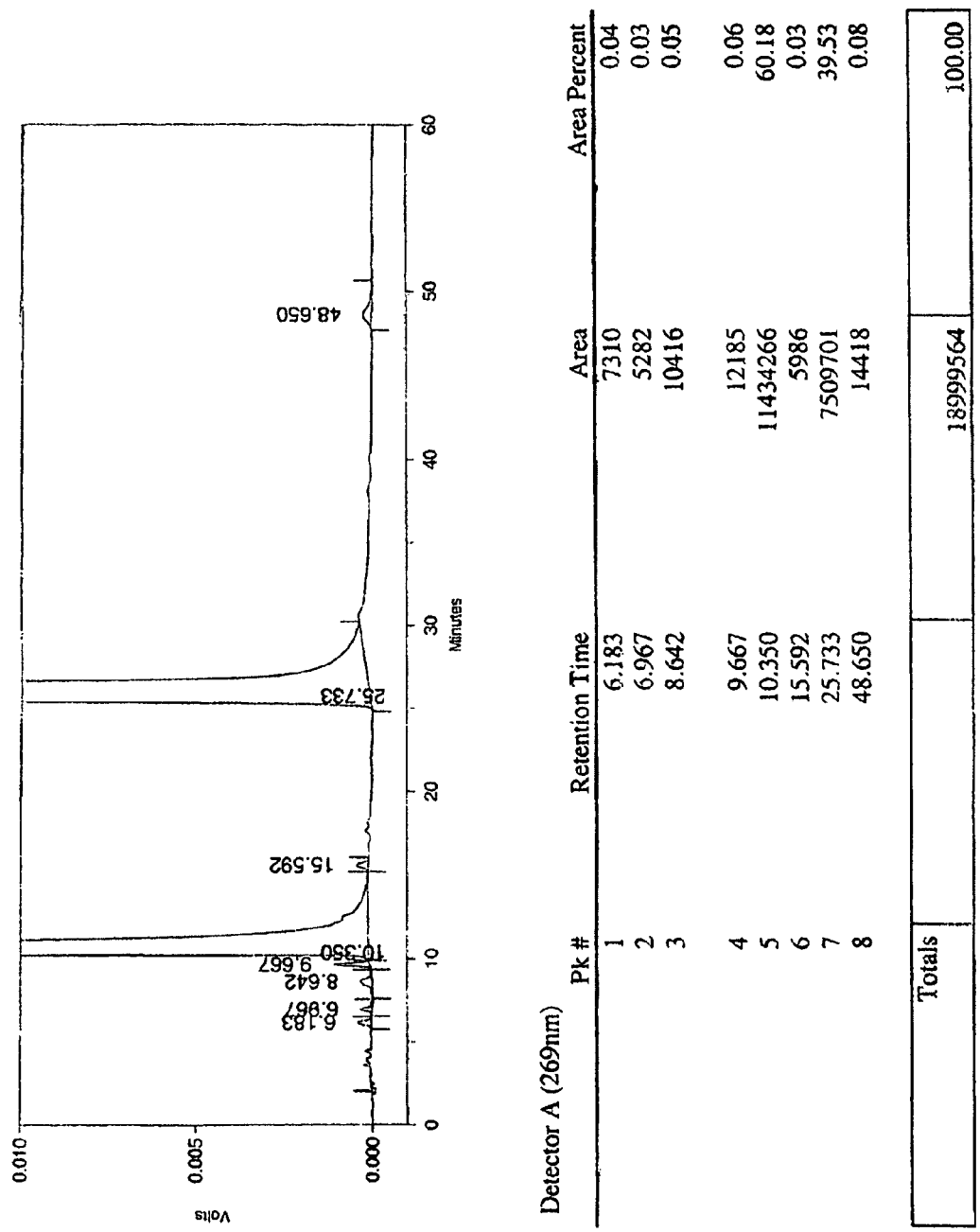
FIG. 1 provides HPLC diagram indicating the purity level of the Imipramine Pamoate obtained from the present invention.

In an embodiment of the present invention, the method can be carried out as a single pot process to improve the yield of the product by minimizing the loss during the intermediate workup step. The yield of the compound has been found to be very high ranging from about 92% to about 98% with purity levels higher than 99.7%. The FIG. 1, HPLC diagram provides the purity level of the compound.

In an embodiment of the present invention, the separation of Imipramine Pamoate from the reaction mixture involves either filtration or distillation depending upon the choice of the solvent.

In an embodiment of the present invention, Imipramine is obtained by treating Imipramine hydrochloride with Sodium hydroxide or commercially available Imipramine can be used is used in the preparation.

In an embodiment of the present invention, solvents for the reaction are selected from a group comprising ethylacetate, dichloromethane, isopropylacetate, methyl ethyl ketone, acetone and combination thereof.

The choice of the above mentioned solvents helps in reducing the impurities like sodium chloride which is otherwise obtained with the other solvents. The synthesis as compared to the prior arts is easily scalable as it comprises simple and cost effective reagents with only two steps. The above said advantages of the present disclosure also makes it economically more feasible.

Figure 2:
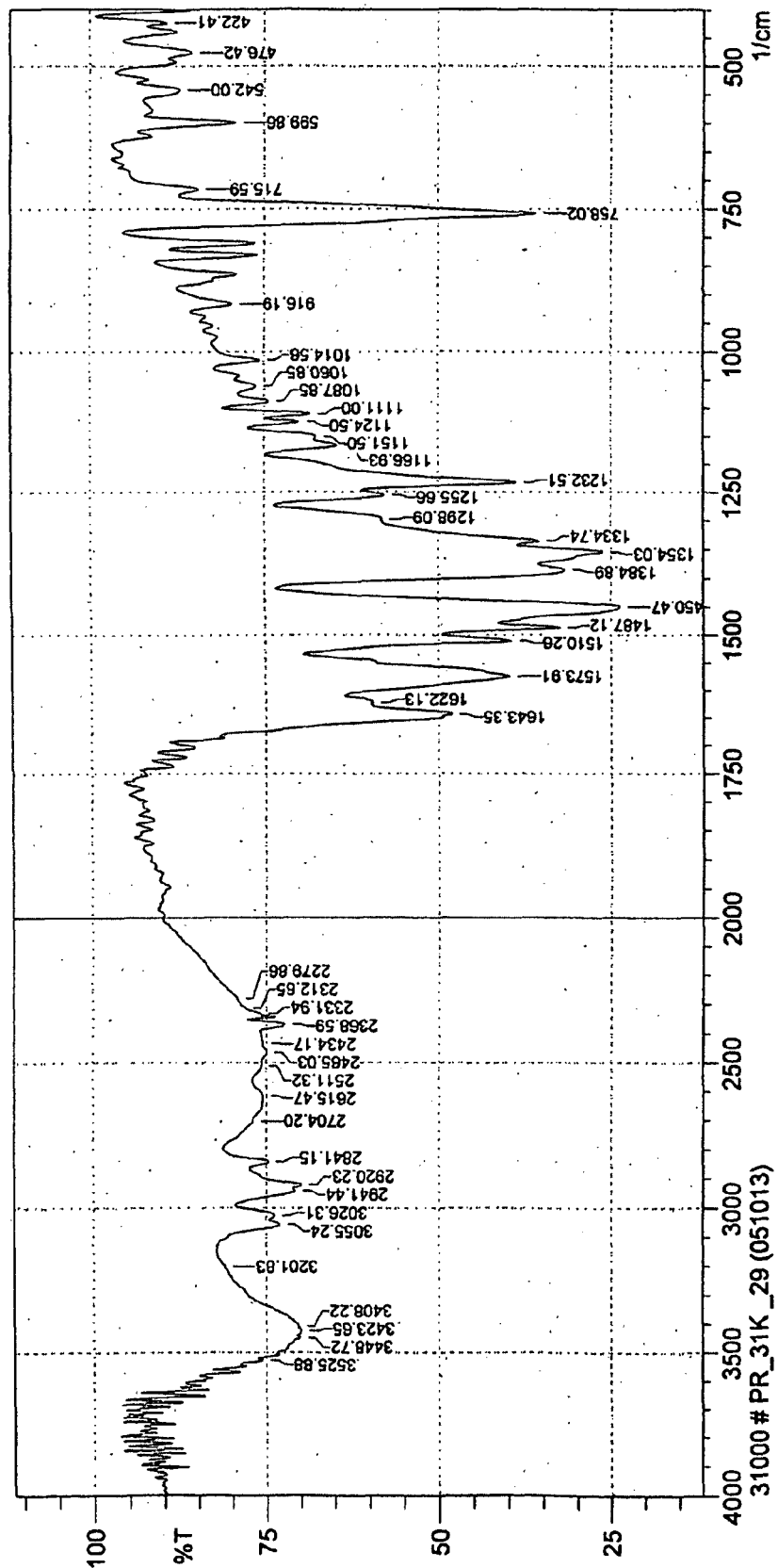
FIG. 2 indicates the Fourier transform infrared spectrum of crystalline form of Imipramine Pamoate of present invention.
Figure 3:
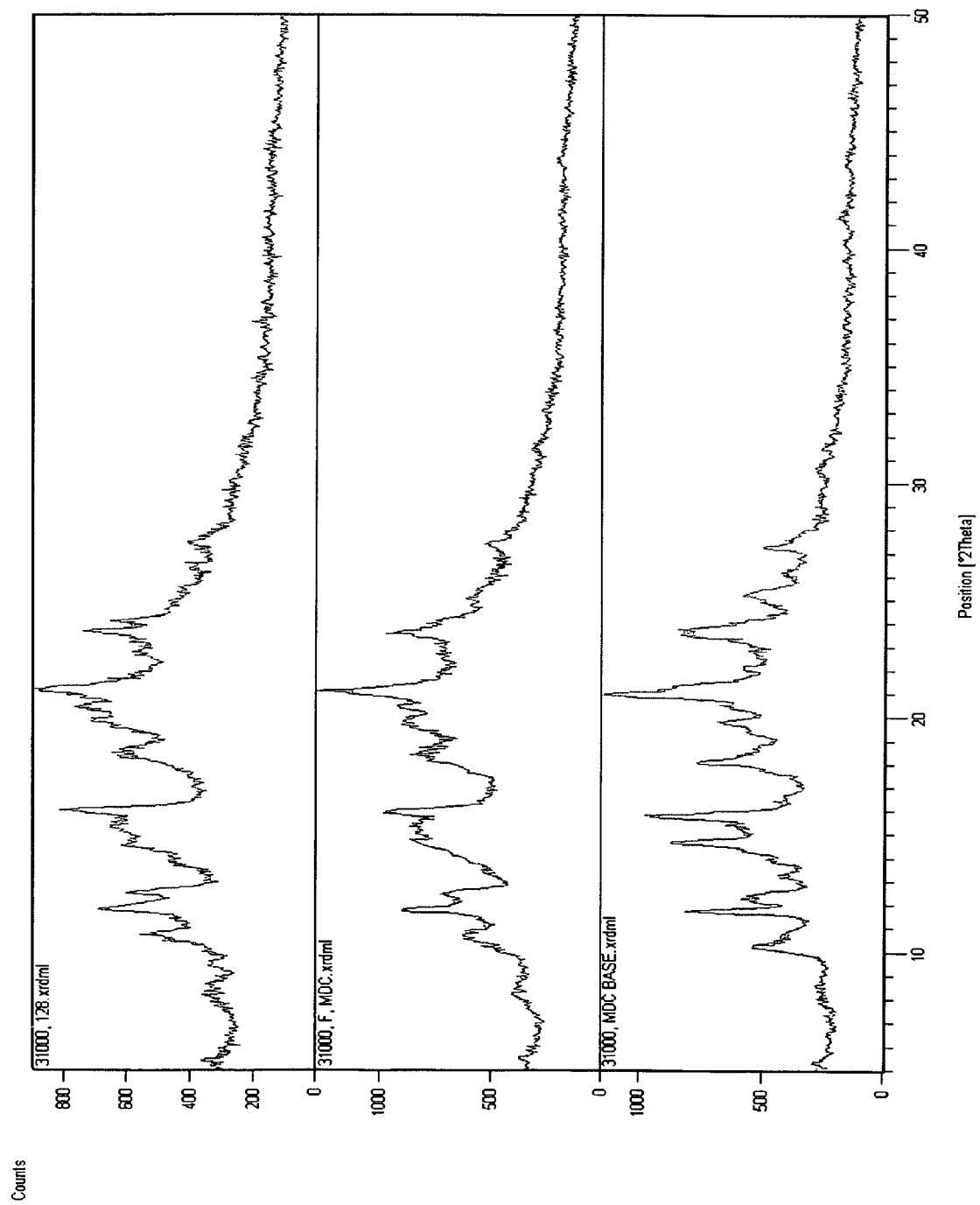
FIG. 3 indicates the X-ray powder diffraction pattern of crystalline form of Imipramine Pamoate of the present invention.
Figure 4:
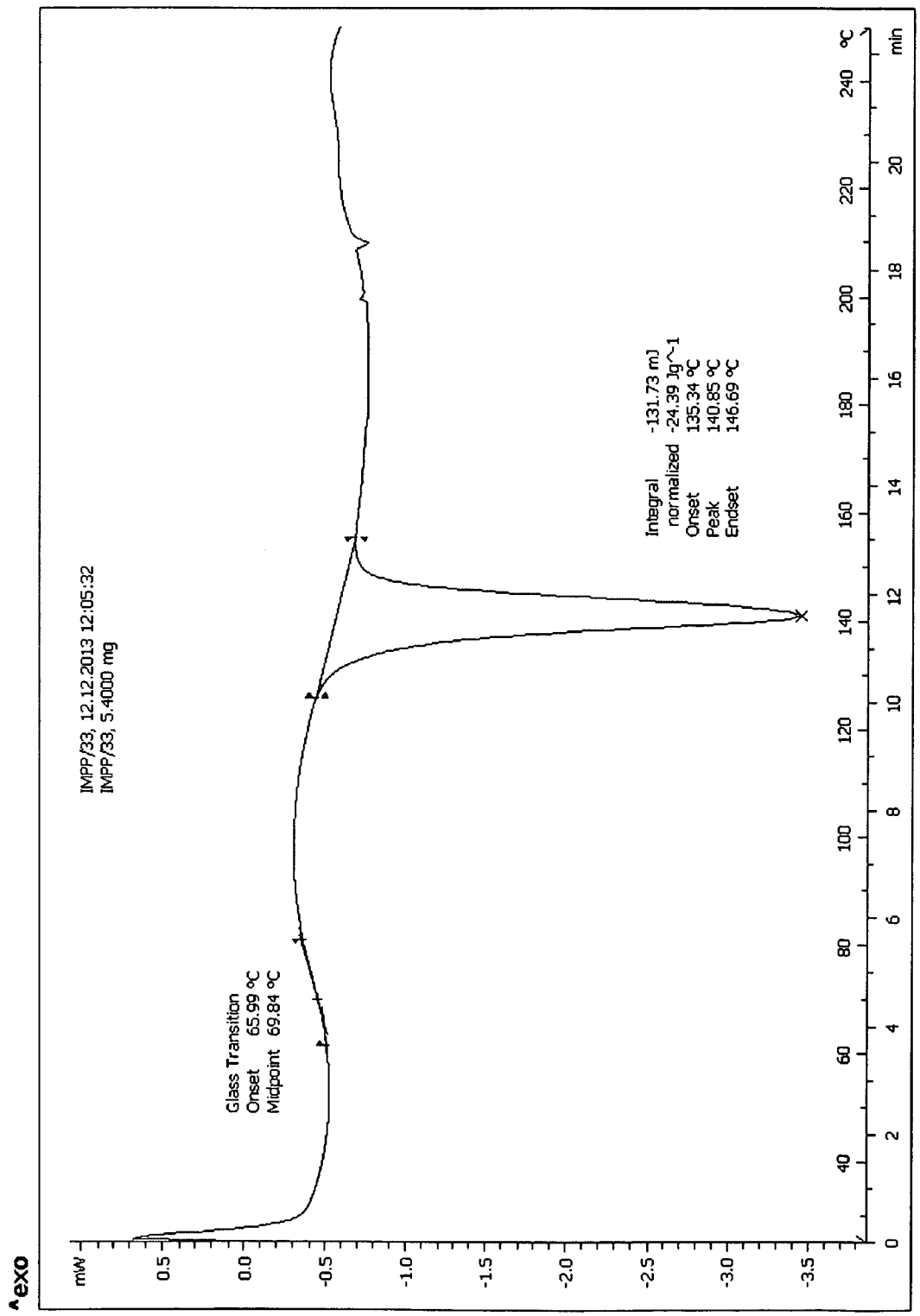
FIG. 4 indicates DSC curve of crystalline form of Imipramine Pamoate of present invention.

Further, it has been characterized that the Imipramine Pamoate of the present invention is a novel polymorphic crystalline form. The X-ray powder diffraction method, Fourier transform spectrum and Differential scanning colorimetry have been utilized to analyse the new polymorphic form (FIGS. 2-4).

In an embodiment of the present invention, the Imipramine Pamoate crystalline solid of the present invention can be formulated as medicaments along with suitable excipients selected from a group comprising fillers, disintegrants, lubricants, glidants, colouring agents and binders; as tablets, capsules or syrups.

A more complete understanding can be obtained by reference to the following specific examples, which are provided for purposes of illustration only and are not intended to limit the scope of the disclosure.

Preparation of Imipramine Pamoate

EXAMPLE 1

To a slurry of Pamoic acid (32.4 g) in ethyl acetate (250 mL) in a clean round bottomed flask, Imipramine (85 g, pre-generated from Imipramine hydrochloride –90 g, sodium hydroxide –18 kg in water, 60-100 mL) solution in ethyl acetate is added maintaining the temperature below 50° C. for 3-4 h. After complete addition, the reaction mixture is stirred at room temperature for about 12-14 h. The bright yellow slurry thus obtained is filtered and washed with ethyl acetate (400 mL) and dried to get Imipramine Pamoate (76 g, 96%) as bright yellow crystalline product.

EXAMPLE 2

To a slurry of Pamoic acid (32.4 g) in ethyl acetate (500 mL) in a clean round bottomed flask, Imipramine (150 g) solution in ethyl acetate is added at such a rate that the temperature remains below 50° C. for 3-4 h. After complete addition, the reaction mixture is stirred at room temperature for about 12-14 h. The bright yellow slurry thus obtained is filtered and washed with ethyl acetate (200 mL) and dried to get Imipramine Pamoate (73 g, 92%) as bright yellow crystalline product.

EXAMPLE 3

To a slurry solution of Imipramine (70 g) in dichloromethane (1000 mL) in a round bottomed flask, Pamoic acid (32.4 g) is added. This reaction mixture is stirred for 16 h at a temperature ranging from about 20-30° C. During which, Imipramine Pamoate almost becomes a clear solution in dichloromethane. The dichloromethane layer is filtered and distilled (about 70-90%). Later, Acetone (750 mL) is added. The bright yellow solid obtained is filtered and dried to get Imipramine Pamoate (76 g, 96%) as bright yellow crystalline product.

Thus the present invention typically provides a low cost, two step method to produce Imipramine Pamoate making use of commonly available solvents and substrates in high yield and purity.

We claim:

1. A method for preparation of Imipramine Pamoate, said method comprising acts of,
   a) reacting Imipramine and Pamoic acid in a solvent and stirring to obtain Imipramine Pamoate solution; and
   b) filtering or distilling followed by precipitating to obtain the Imipramine Pamoate from the solution.

2. The method as claimed in claim 1, wherein the method is a single or multiple pot preparation.

3. The method as claimed in claim 1, wherein the Pamoic acid and the Imipramine are taken in a ratio ranging from about 2:1 to about 4:1.

4. The method as claimed in claim 1, wherein the solvent is selected from a group comprising dichloromethane, ethylacetate, isopropylacetate, methyl ethyl ketone, acetone and combination thereof.

5. The method as claimed in claim 1, wherein the stirring is carried out for a period ranging from about 12 hr to about 16 hr.

6. The method as claimed in claim 1, wherein the stirring is carried out at a temperature ranging from about 20° C. to about 50° C.

7. The method as claimed in claim 1, wherein the Imipramine Pamoate is filtered if the solvent is the ethylacetate.

8. The method as claimed in claim 1, wherein the Imipramine Pamoate is precipitated by acetone or ethyl acetate if the solvent is the dichloromethane.

9. The method as claimed in claim 1, wherein the Imipramine Pamoate is of purity ranging from about 99.7% to about 99.9% and yield ranging from about 90% to about 99%.

10. The method as claimed in claim 2, wherein the method is a single pot preparation.

* * * * *